United States Patent [19]

Lee et al.

[11] Patent Number: 5,135,964
[45] Date of Patent: Aug. 4, 1992

[54] ULTRAVIOLET CURED PEELABLE FILM AND METHOD THEREFOR

[75] Inventors: Min-Shiu Lee, Spring Valley; John Gleason, Dayton; Robert A. Taller, Centerville, all of Ohio

[73] Assignee: Becton, Dickinson and Company, Franklin Lakes, N.J.

[21] Appl. No.: 672,246

[22] Filed: Mar. 20, 1991

Related U.S. Application Data

[62] Division of Ser. No. 179,354, Apr. 8, 1988, Pat. No. 5,030,665.

[51] Int. Cl.$^5$ .................. C08F 283/04; C08F 2/50
[52] U.S. Cl. .................................... 522/96; 525/455; 525/454; 526/264
[58] Field of Search .......................................... 522/96

[56] References Cited

U.S. PATENT DOCUMENTS 4,483,759  11/1984  Szycher et al. ...................... 522/20

FOREIGN PATENT DOCUMENTS 3437531  4/1985  Fed. Rep. of Germany ........ 522/96

Primary Examiner—Marion E. McCamish
Assistant Examiner—Susan Berman
Attorney, Agent, or Firm—Richard E. Brown

[57] ABSTRACT

Radiation cured peelable film useful as a surgical drape or wound dressing includes a copolymer of a vinyl monomer and an acrylate capped polyurethane prepolymer. The cured film may be prepared by casting a mixture of the vinyl monomer, prepolymer and a photoinitiator onto a surface as a liquid film and exposing the liquid film to ultraviolet light.

6 Claims, No Drawings

ULTRAVIOLET CURED PEELABLE FILM AND METHOD THEREFOR

This is a division of application Ser. No. 07/179,354 filed Apr. 8, 1988, now U.S. Pat. No. 5,030,665, issued Jul. 9, 1991.

BACKGROUND OF THE INVENTION

1. Field of the Invention

This invention relates to films, and more specifically, relates to a film forming liquid which is ultraviolet curable to an in situ formed surgical drape or wound dressing.

2. Background of the Invention

Conventional surgical drapes and wound dressings are composed of preformed films which may be solid but are generally porous. Such films are conventionally referred to as continuous and are usually adhered to the skin by a suitable adhesive. Several disadvantages result from this procedure. For example, preformed drapes often do not form a tight continuous seal with the skin so that avenues are available for bacterial penetration. Further, preferred films are difficult to adhere over irregular anatomical contours such as hands and knees. Care must be taken that nothing other than the drape (as, for example, a sleeve of a surgical gown) comes in contact with the adhesive prior to emplacement of the drape.

Surgical drapes which are applied as a solution in an appropriate solvent and subsequently cured by evaporation of the solvent are known. Cardarelli et al., in U.S. Pat. No. 4,374,126 discloses an antimicrobial film of a polyacrylic acid crosslinked with urea prepared by casting a solvent solution of the ingredients and evaporating the solvent. Good antimicrobial effect, transpiration, skin adherence and resistance to body fluids while being removable with soap and water are described.

U.S. Pat. No. 4,542,012 to Dell discloses an antimicrobial composition applied to the skin as a solvent solution which forms a film upon solvent evaporation. The composition includes an isocyanate-terminated polyurethane prepolymer linked to an isocyanate-terminated copolymer of an acrylate and N-vinylpyrrolidone by a chain extender. Iodine complexed with the polyvinylpyrrolidone is included as an antiseptic.

Burleigh, in U.S. Pat. No. 4,613,544 discloses a sheet material consisting of a backbone polymeric membrane matrix having transmembrane passageways which are filled with a hydrophilic polyoxyalkylene polyurethane applied as a prepolymer and cured in situ by heat or light.

Ultraviolet curing of acrylate terminated polyurethanes is disclosed by Szycher et al. in U.S. Pat. No. 4,483,759.

Several of the disadvantages of adhesively adhered preformed drapes have been addressed by these inventions, but deficiencies remain. The solvents used for casting may be irritative to the skin, and may require a long time for evaporation. In particular, solvent evaporation in a medical environment such as an operating room may be both a health hazard and a fire hazard. It is toward the overcoming of these deficiencies that this invention is directed.

SUMMARY OF THE INVENTION

A radiation cured film is formed of a copolymer of a vinyl monomer and a prepolymer of a polyurethane oligomer and oxyalkyl acrylate terminal groups. Preferred vinyl monomers are acrylates and vinyl lactams. The oligomer may be formed of a polyisocyanate, preferably a diisocyanate, a polyol, preferably a polyester-polyol, and a chain extending diol. The most preferred prepolymer is the reaction product of isophorone diisocyanate, polycaprolactone and 1,4-butanediol. The most preferred vinyl monomer is N-vinyl pyrrolidone.

In another aspect of the invention, a method to form a peelable film includes casting a mixture of the vinyl monomer, the prepolymer and a photoinitiator onto a surface to form a liquid film and curing the liquid film by exposure to electromagnetic radiation, preferably ultraviolet (UV) light. In the present disclosure, the term peelable is understood to mean that the film is removable in one piece with substantially no tearing or fragmentation, and the terms casting and curing respectively mean forming a liquid film on a surface and causing the liquid film to polymerize and solidify.

The cured film of the invention is ideal for use as an in situ cured liquid drape or wound dressing and overcomes problems associated with prior art, preformed wound dressings. The present invention is applied to a patient's skin as a liquid and then cured to form a film. Thus, it flows freely into all depressions of the skin so that, when cured, no channels remain to provide access routes for bacteria. This skin-tight film is achieved without the use of a toxic or flammable solvent which must be removed as required in prior art films. Because the films of the invention are formed without solvent and are removable in one piece by simple peeling, cleanliness in a medical environment is enhanced. Curing of the film of the invention may be carried out in a matter of seconds with a hand held ultraviolet lamp, a major advantage in an operating room where solvent evaporation is time consuming and a health hazard.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The present invention provides a continuous film prepared by curing a layer of a liquid formulation with ultraviolet light. The cured film has a balance of tensile strength, modulus, elongation and slit tear strength which makes it ideal as a surgical drape or wound dressing which adheres firmly to the skin but which is easily removed by peeling.

In this disclosure, the following abbreviations are used.
PCL—polycaprolactone
PTMEG—polytetramethylene ether glycol
PPEG—polypropylene ether glycol
BDO—1,4-butanediol
IPDI—isophorone diisocyanate
HEA—hydroxyethyl acrylate
HEMA—hydroxyethyl methacrylate
IDA—isodecyl acrylate
2-EHA—2-ethylhexyl acrylate
THFMA—tetrahydrofurfuryl methacrylate
NVP—N-vinyl pyrrolidone
DMF—dimethylformamide MEK—methyl ethyl ketone The liquid formulation of the invention is a mixture of a vinyl monomer and a prepolymer having a polyurethane oligomer and oxyalkyl acrylate terminal groups. The polyurethane oligomer may be formed from a polyisocyanate, a polyol and a chain extending diol. Preferred polyisocyanates are aromatic, aliphatic or alicyclic diisocyanates, such as diphenylmethane-4,4'-diisocyanate, diphenylmethane-3,3'-diisocyanate, IPDI, dicyclohexylmethane-4,4'-diisocyanate, and hexamethylene diisocyanate. The most preferred diisocyanate is IPDI.

The polyol component may be a polyether glycol such as polyethylene oxide, PPEG and PTMEG. Preferred polyols are polyester glycols, such as polyethylene adipate and PCL. Particularly preferred polyester glycols have a molecular weight from about 500 to 5000. The most preferred polyol is PCL of molecular weight about 2000.

The chain extender may be a low molecular weight branched or unbranched diol of up to 10 carbon atoms or mixtures thereof. Representative nonlimiting examples of chain extenders are BDO; ethylene glycol; diethylene glycol; triethylene glycol; 1,2-propanediol; 1,3-propanediol; 1,6-hexanediol; 1,4-bis-hydroxymethyl cyclohexane, and hydroquinone dihydroxyethyl ether. Preferred chain extenders are 1,6-hexanediol and BDO.

Reaction of the diisocyanate, polyol and diol to give the oligomer may be carried out by heating the reactants for a suitable time, either neat or preferably in a suitable solvent, such as MEK. A conventional catalyst, such as dibutyl tin dilaurate, may be used to accelerate the reaction. The ratio of the reagents may be chosen such that the oligomer is capped with isocyanate groups. Thus, any ratio may be used which has about one equivalent more diisocyanate than the combined equivalents of polyol and diol. For example a suitable oligomer may be formed from 6 equivalents of diisocyanate reacted with about 0.5 to 3 equivalents of polyol and about 4.5 to 2 equivalents of diol. Most preferably, the oligomer contains about 1.0 to 1.2 equivalents of polyol and 4.0 to 3.8 equivalents of diol. An example of a typical procedure for oligomer synthesis is given in Example I, however, various modifications of this procedure set forth therein are well-known to those skilled in the art.

A prepolymer having oxyalkyl acrylate terminal groups may be prepared by reacting the isocyanate caps of the oligomer and a suitable hydroxylated acrylate. Suitable hydroxylated acrylates are, for example, hydroxyethyl, hydroxypropyl and hydroxybutyl acrylates and methacrylates, although it is evident that a wide variety of other hydroxylated acrylate derivatives may be used. Preferred hydroxylated acrylates for oxyalkyl capping of the prepolymer are HEA and HEMA.

Reaction of the hydroxylated acrylate and the isocyanate caps on the oligomer may conveniently be carried out merely by adding the acrylate to the solvent solution of the oligomer and heating for a suitable period. If desired, recovery of the prepolymer from the solvent may be carried out by any conventional technique, as for example, by solvent evaporation or by dilution with a solvent to precipitate the prepolymer, followed by filtration and drying. Preferably, the prepolymer in the solvent is merely diluted with the vinyl monomer, as described below.

In some cases, it may be desirable to crosslink the prepolymer. A crosslinking agent may be added to the mixture of diisocyanate, polyol and diol in order to crosslink the oligomer to any desired level. Alternatively, the crosslinking agent may be mixed with the hydroxylated acrylate. Any conventional crosslinking agent as known in the art of polyurethane synthesis may be used. Particularly suitable crosslinking agents are triols, as for example, trimethylol propane. The quantity of crosslinking agent may be from 0 to about 10 weight percent of the polyol. It is understood that when the crosslinking agent is part of the oligomer, the total equivalents of polyol, diol and triol crosslinking agent is one less than the equivalents of diisocyanate.

Although a film of the prepolymer may itself be cast and cured to give a peelable film of the invention, it is preferred to form a mixture of the prepolymer and a vinyl monomer prior to casting. The vinyl monomer serves to reduce the viscosity of the prepolymer for convenience in casting, and becomes part of the polymer matrix of the film upon curing.

A wide variety of vinyl monomers or mixtures thereof may be mixed with the prepolymer, as, for example, IDA, HEA, THFMA, HEMA, 2-EHA, vinyl acetate, 1,4-butanediol diacrylate, trimethylolpropane triacrylate, 2-phenylethyl methacrylate, and the like. Preferred vinyl monomers are lactams substituted on the nitrogen atom with an olefinic group, such as a vinyl or isopropenyl group. The lactam may have 4, 5 or 6 carbon atoms and thus, for example, may be a pyrrolidone, piperidone, piperazinedione or caprolactam.

The preferred vinyl monomer is NVP, neat or mixed with one or more additional vinyl monomers, as IDA, 2-EHA or HEA. The weight percentage of vinyl monomers in the mixture to be cast and cured may be about 1 to 50%, preferably about 25-40%.

A photoinitiator may be added to the mixture to catalyze the copolymerization of the acrylate terminated prepolymer and the vinyl monomer. Any conventional photoinitiator as known in the art may be used. Examples of suitable photoinitiators are given in Szycher et al., supra, and selection of a suitable photoinitiator is well within the purview of one skilled in the art. Particularly useful photoinitiators are the Irgacure TM cyclohexyl phenyl ketone derivatives (Ciba Geigy).

An antimicrobial agent may also be added to the mixture prior to casting and curing. Any antimicrobial agent which is substantially stable to ultraviolet light and which may be released slowly from the cured film may be used. Exemplary of suitable antimicrobial agents are povidone iodine, chlorohexidene or chlorohexideneiodine complex. The quantity of antimicrobial agent to be added may be from about 1 to 10; preferably 2 to 6 weight percent.

In order to obtain the desired film properties, conventional additives such as flow aids, flatting agents, plasticizers, polymerization inhibitors, heat stabilizers and surface cure modifiers may sometimes be added to the formulation prior to casting and curing. A suitable surface cure modifier, for example is TMPTMP, trimethylol propane tri-(3-mercaptopropionate).

Casting is a conventional operation, and in the present disclosure may be performed by dipping, spraying, spreading or any other suitable means. Preferably, the mixture is cast neat onto a suitable surface, as, for example, silicone release paper or a glass plate. In the most preferred embodiment of the invention, the mixture is cast onto the skin of an animal, for example, over a wound or surgical incision site of a human being. The cast liquid films may be adjusted to any desired thickness by conventional means, as a doctor knife, and may be from about 0.1 to 2.5 mm, preferably about 10μ to 1.0 mm thick.

Curing may be carried out merely by exposing the cast liquid film to electromagnetic radiation, preferably UV light. A conventional UV lamp may be used, as, for example, a Conrad-Hanovia Model 45080 (Conrad-Hanovia Inc., Newark, N.J.) or a Blak-Ray Model UVL-56 (Ultraviolet Products, Inc., San Gabriel, Calif.). Surface cure occurs almost instantaneously. The length of exposure required to bulk cure the liquid film depends on the thickness of the film. In general, films of from about 25μ to 1.0 mm in thickness are bulk cured in about 15 to 120 sec. when the lamp is positioned about 15 cm. from the film. Parameters of curing such as lamp intensity, duration of exposure and distance of the film from the lamp are well understood by those skilled in the art and no further details are needed.

The cured films of the invention may be evaluated for their tensile strength, modulus, elongation and tear strength by ASTM methods well known in the art. The testing results below are given in pounds per square inch (psi) and pounds per linear inch (pli), which are equivalent to 0.07 kg/cm$^2$ and 0.178 kg/cm respectively. Tensile strength is a measure of the force, generally given in psi, required to break a polymer. Elongation is a measure of the ability of a polymer to stretch without breakage, and is generally reported as a percentage of an initial value. The term modulus defines the force (in psi) required to stretch a polymer to a given percentage of elongation. Tensile, modulus and elongation may be measured by ASTM procedure D 638 using an Instron Universal Testing instrument, Model 1122. Slit tear strength is the force (in pli) required to propagate a tear in a film along the line of a previously introduced slit, and may be tested by ASTM procedure, D 1938. Die C tear is the force (in pli) required to initiate a tear at a previously introduced notch, and may be tested by ASTM procedure D 1004.

It has been found that tear strength is an important property for determining whether a film is suitable for use as a peelable drape or wound dressing. In general, a slit tear strength of about 5-50 pli combined with a die C tear strength of about 45-250 pli confers peelability to the cured film of the invention. Preferred films have slit tear and die C tear strengths of about 20-45 and 100-200 pli respectively. Broad ranges of tensile, and elongation which, when combined with the tear strengths given above, define peelable films of the invention may be 1,000-10,000 psi and 150%-400% respectively. Modulus is a less important parameter, and may be from 10-1,000 psi at 5% elongation.

Representative nonlimiting examples of peelable films of the invention are given in Table I. The films were prepared as described in Example I from the indicated commercial polyol, IPDI, BDO and HEA in the equivalent ratio 1:6:4:1.

TABLE I

| POLYOL | Tensile psi | Modulus psi @ 5% | Elongation % | Tear Strength, pli. Slit | Die C |
|---|---|---|---|---|---|
| PTMEG$^a$ | 2800 | 880 | 280 | 10 | 190 |
| PPEG$^b$ | 1500 | 465 | 215 | 11 | 120 |
| (linear polyester)$^c$ | 2100 | 730 | 280 | 24 | 200 |
| PCL$^d$ | 2000 | 505 | 320 | 46 | 160 |

$^a$Teracol ™ 2000 ... E. I. Du Pont de Nemours and Co. Wilmington, DE
$^b$NIAX ™ PPG 2025 ... Union Carbide, Tarrytown, NY
$^c$Ruco ™ S-1059-55 ... Ruco Polymer Corp., Hicksville, NY
$^d$TONE ™ 0240 ... Union Carbide, Danbury, CT For comparison purposes, cured films were prepared from various commercially available acrylate capped polyurethane prepolymers copolymerized with NVP by the procedure of Example I. The composition and properties of these films are given in Table II.

TABLE II

| COMPOSITION$^a$ | A$^b$ | B | C | D | E | F | G | H | I | J | K | L | M | N |
|---|---|---|---|---|---|---|---|---|---|---|---|---|---|---|
| COMPOSITION, WEIGHT PERCENT | | | | | | | | | | | | | | |
| UVITHANE ™ 782 | 100 | 100 | 70 | 70 | 70 | 70 | 60 | 60 | 60 | 70 | 70 | 70 | 50 | 40 |
| CHEMPOL ™ 19-4833 | — | — | — | — | 15 | — | 10 | 5 | 15 | 15 | 10 | — | — | 5 |
| PHOTOMER ™ 4770 | — | — | — | — | — | 15 | 10 | 5 | 15 | 15 | — | 10 | — | 5 |
| AMICON ™ LV-2321-59 | — | — | — | — | — | — | — | — | — | — | — | — | 20 | 20 |
| NVP | — | — | 30 | 30 | 15 | 15 | 20 | 30 | 10 | — | 20 | 20 | 30 | 30 |
| DEAP$^a$ | 2 | — | 2 | — | — | — | — | — | — | — | — | — | — | — |
| IRGACURE ™ 651 | — | 2 | — | 2 | 2 | 2 | 2 | 2 | 2 | 2 | 2 | 2 | 2 | 2 |
| PROPERTIES | | | | | | | | | | | | | | |
| TENSILE psi | 2400 | 2200 | 310 | 400 | 1700 | 1600 | 2700 | 500 | 1000 | 620 | 3100 | 2800 | 2500 | 1900 |
| MODULUS 5% psi | 24 | 23 | 30 | 32 | 59 | 28 | 65 | 29 | 50 | 23 | 55 | 31 | 70 | 120 |
| ELONGATION % | 175 | 190 | 100 | 120 | 115 | 110 | 110 | 110 | 83 | 100 | 150 | 145 | 127 | 107 |
| TEAR (Slit) pli | 6 | 0 | 0 | 0 | 0 | 0 | 3 | 0 | 0 | 0 | 1 | 3 | 3 | 6 |
| TEAR (Die C) pli | 130 | 78 | 16 | 8 | 50 | 26 | 32 | 30 | 26 | 17 | 50 | 120 | 50 | 49 |

$^a$acetophenone based photoinitiator - Union Carbide
$^b$Although this formulation has physical properties which would make it peelable, its viscosity was too high for effective casting.

It is seen that these films exhibit adequate tensile strength and elongation, but tear strength is very low. In general, these compositions do not lead to peelable films.

In order to simulate actual use conditions, liquid films may be cast onto pig skin and cured as given in Example II and their physical properties and peelability from the pig skin determined. Table III gives data for three films prepared from IPDI, HEA, BDO, Irgacure ™ 184 and the indicated polyols and vinyl monomers. The films of Table III are all peelable.

TABLE III

| Composition | Tensile psi | Modulus psi @ 5% | Elongation % | Tear Strength, pli Slit | Die C |
|---|---|---|---|---|---|
| 1 TONE ™ 0305, 0.25 eq. TONE ™ 0240, 0.75 eq. 2-HEA, 25.2 wt. % | 1568 | 33 | 233 | 7 | 67 |

TABLE III-continued

| Composition | Tensile psi | Modulus psi @ 5% | Elongation % | Tear Strength, pli | |
|---|---|---|---|---|---|
| | | | | Slit | Die C |
| NVP, 14.0 wt. % | | | | | |
| 2 NIAX ™ PPG 2025 1.0 eq. | 1034 | 180 | 225 | 17 | 93 |
| IDA, 9.8 wt. % | | | | | |
| NVP 26.4 wt. % | | | | | |
| 3 TONE ™ 0240, 1.0 eq. | 2298 | 390 | 285 | 34 | 159 |
| IDA, 9.8 wt. % | | | | | |
| THFMA, 4.9 wt. % | | | | | |
| NVP 25.0 wt. % | | | | | |

Likewise, in live animal testing of various cured films of the invention in accordance with Example III, the films of Table III are peelable.

EXAMPLE I

General Procedure for Synthesis of Cured Films

A mixture of IPDI (6 equivalents), BDO (4 equivalents), 2,000 molecular weight polyol (1 equivalent), and 0.05% stannous octoate in MEK at 90% solids was heated and stirred at 70° C. until oligomer formation was 98–105% complete. The mixture was cooled to 50° C. and 1 equivalent of HEA was added. The mixture was stirred until the precent of free isocyanate was 0.5 or less to give a prepolymer having oxyalkyl acrylate terminal groups. If necessary to maintain a workable viscosity some of the reactive diluent described below, may be added during a propolymer formation.

The prepolymer was combined with 2 weight percent of Irgacure ™, and sufficient NVP, optionally containing one or more other vinyl monomers, to give a total solid content of about 60%. Up to 10 weight percent of a reactive diluent, such as IDA, may be added to reduce viscosity. The mixture was stirred until all components were homogeneously dispersed, set aside to allow all bubbles to escape and cast onto silicone release paper. The thickness of the film was adjusted to 50μ with a doctor knife and cured by exposure to the Conrad-Hanovia lamp until a tackless surface was obtained, generally about 1 second. The cured film was removed from the release paper for evaluation of physical and mechanical properties.

EXAMPLE II

General Procedure for Curing Onto Pig Skin

A belly section of pig skin was cleaned and degreased by wiping several times with cotton balls saturated with acetone and finally with alcohol. Cured films were formed on the pig skin by the procedure of Example I and allowed to remain on the skin in ordinary light for several hours to determine whether oil blooming to the surface of the skin would cause the films to release from the skin. Data obtained for representative films is given in Table III.

EXAMPLE III

Live Animal Testing of Peelability

A 40–45 pound pig was anaesthetized, and a belly section was washed and shaved with electric clippers. Liquid films, prepared in accordance with Example I, were adjusted to a thickness of about 0.6 mm and were cured in situ with the Blak-Ray UVL 56 (2 minutes exposure) and Blak-Ray B-100A (1 minute exposure) lamps. The cured films had tensile strengths of 2500–2700 psi, elongation of 230–330%, slit tear strengths of 16–44 pli and Die C tear strengths of 70–170 pli. All films easily peeled from the pig skin intact.

What is claimed is:

1. A method for forming a peelable film on a surface comprising:
   a) preparing a mixture comprising a photoinitiator, an olefinically substituted lactam and a prepolymer, said prepolymer including a polyurethane oligomer from the reaction of a diisocyanate, a polyol and a chain extending diol, said oligomer having an oxyalkyl acrylate terminal group;
   b) casting said mixture onto a surface to form a liquid film; and
   c) exposing said liquid film to ultraviolet light whereby said vinyl lactam and said prepolymer copolymerize to form a peelable film on said surface said film having a slit tear strength of about 5 to 50 pounds per linear inch and a die C tear strength of about 45 to 250 pounds per linear inch.

2. The method of claim 1 wherein said lactam is N-vinyl pyrrolidone.

3. The method of claim 1 wherein said diisocyanate is an alicyclic diisocyanate.

4. The method of claim 1 wherein said polyol is a polyester diol.

5. The method of claim 1 wherein said diol has from two to ten carbon atoms.

6. A method for forming a peelable film on a surface comprising:
   a) preparing a mixture comprising a photoinitiator, N-vinyl pyrrolidone and a prepolymer, said prepolymer including a polyurethane oligomer from a reaction of a diisocyanate, a polyester diol and a chain extending diol of no more than ten carbon atoms, said oligomer having an oxalkyl acrylate terminal group;
   b) casting said mixture onto a surface to form a liquid film; and
   c) exposing said liquid film to ultraviolet light whereby said N-vinyl pyrrolidone and said prepolymer copolymerize to form a peelable film on said surface said film having a slit tear strength of about 5 to 50 pounds per linear inch and a die C tear strength of about 45 to 250 pounds linear inch.

* * * * *